(12) United States Patent
Hensen et al.

(10) Patent No.: US 6,235,696 B1
(45) Date of Patent: May 22, 2001

(54) HEAVILY FOAMING DETERGENT MIXTURES CONTAINING FATTY ACID POLYGLYCOL ESTER SULPHATES

(75) Inventors: Hermann Hensen, Haan; Ullrich Bernecker, Huertgenwald; Joerg Kahre, Leichlingen; Werner Seipel, Hilden; Holger Tesmann, Juechen; Thomas Engels, Frechen; Hans-Christian Raths, Monheim; Bernd Fabry, Korschenbroich, all of (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/486,340

(22) PCT Filed: Aug. 17, 1998

(86) PCT No.: PCT/EP98/05210
   § 371 Date: May 22, 2000
   § 102(e) Date: May 22, 2000

(87) PCT Pub. No.: WO99/10461
   PCT Pub. Date: Mar. 4, 1999

(30) Foreign Application Priority Data

Aug. 25, 1997 (DE) .............................. 197 36 906
Sep. 25, 1997 (DE) .............................. 197 41 911

(51) Int. Cl.⁷ .................................................. C11D 17/00
(52) U.S. Cl. ......................... 510/235; 510/426; 510/427; 510/428; 510/492
(58) Field of Search .................... 510/235, 426, 510/427, 428, 492

(56) References Cited

U.S. PATENT DOCUMENTS 4,412,944   11/1983   Panzer et al. .

FOREIGN PATENT DOCUMENTS

| 1 498 692 | 1/1978 | (GB) . |
| 06293620 | 10/1994 | (JP) . |
| WO 95/23204 | 8/1995 | (WO) . |

OTHER PUBLICATIONS

J. Falbe (Ed.), "Surfactants in Consumer Products", Springer Verlag, Berlin, 1987, pp. 54–124.

J. Falbe, et al. (Ed.), "Katalysatoren, Tenside und Mineralöladditive (Catalysts, Surfactants and Mineral Oil Additives)", Thieme Verlag Stuttgart, 1978, pp. 123–217 DIN 53902, Part 1.

*Primary Examiner*—Necholus Ogden
(74) *Attorney, Agent, or Firm*—John E. Drach; Aaron R. Ettelman

(57) ABSTRACT

Highly foaming detergent mixtures comprising: (a) at least one fatty acid polyglycol ester sulfate of the general formula (I):

$$R^1COO(AO)_xSO_3X \qquad (I)$$

wherein $R^1CO$ represents an acyl group and $R^1$ is selected from the group consisting of linear, branched, saturated and unsaturated chains having from about 6 to about 22 carbon atoms, x is an integer having a value of from 1 to 3, each AO independently represents a $CH_2CH_2O$, $CH_2CH(CH_3)O$ or $CH(CH_3)CH_2O$ group, and X is selected from the group consisting of an alkali metal, an alkaline earth metal, ammonium, an alkylammonium, an alkanolammonium or a glucammonium; and (b) at least one additional surfactant selected from the group consisting of anionics, nonionics, cationics, amphoterics and zwitterionics are disclosed. The disclosed detergent mixtures exhibit advantageous foaming performance and a high level of foam stability even in the presence of hard water and/or oil.

21 Claims, No Drawings

HEAVILY FOAMING DETERGENT MIXTURES CONTAINING FATTY ACID POLYGLYCOL ESTER SULPHATES

CROSS-REFERENCE TO RELATED APPLICATIONS

This application is a 35 U.S.C. §371 national stage application based upon International Application no. EP98/05210, filed Aug. 17, 1998.

FIELD OF THE INVENTION

This invention relates to high-foaming detergent mixtures containing fatty acid polyglycol ester sulfates with a low degree of alkoxylation and to the use of these substances as foam boosters for surfactant mixtures.

PRIOR ART

In a number of surfactant applications, consumers are looking for a high foaming capacity. For example, a shampoo which does not produce enough of a creamy, stable foam during shampooing has no chance of success of the market. The same applies to manual dishwashing detergents, even though a direct connection between foaming capacity and cleaning performance cannot be established at all in many cases. Although a manufacturer of such products will mainly be concerned with developing formulations which satisfy performance requirements, for example in regard to cleaning and dermatological compatibility, he still has to take foaming behavior into account. Now, not all surfactant mixtures which perform satisfactorily and are economical in use are distinguished by satisfactory foaming behavior. Although, in the one case, the basic foam has sufficient height, it collapses rapidly. In the other case, the exact opposite occurs, i.e. although the initial foaming behavior tends more to be average, the foam remains stable for a long time. Even if these properties could be advantageously combined with one another, it would be found that the mixtures would not tolerate water hardness or the presence of oil. Accordingly, the number of surfactant combinations which meets this complex requirement profile tends to be small which explains why the same formulations are always found on the market. One way of overcoming this problem would be to provide surfactant formulations with additives, so-called foam boosters, which favorably influence the foam properties of the mixtures. A typical group of compounds which could be used for this purpose are the fatty acid alkanolamides but unfortunately they have the disadvantage that they do not possess any surfactant properties of their own, i.e. for example make no contribution to the cleaning effect, and in addition are still suspected of containing traces of nitrosamines which is totally inappropriate for applications where the preparations come into contact with the human skin.

Accordingly, the complex problem addressed by the present invention was to provide surface-active preparations which would be free from the disadvantages mentioned above. In particular, the object of the invention was to find foam boosters which would improve both the basic foam and the foam stability of a large number of surfactants, even in the presence of water hardness and oil.

BRIEF SUMMARY OF THE INVENTION

The present invention relates to high-foaming detergent mixtures containing
(a) fatty acid polyglycol ester sulfates corresponding to formula (I):

$$R^1COO(AO)_xSO_3X \quad (I)$$

in which $R^1CO$ is a linear or branched, saturated or unsaturated acyl group containing 6 to 22 carbon atoms, x is a number with an average value of 1 to 3 and AO represents a $CH_2CH_2O$, $CH_2CH(CH_3)O$ and/or $CH(CH_3)CH_2O$ group and X is an alkali metal and/or alkaline earth metal, ammonium, alkylammonium, alkanolammonium or glucammonium, and
(b) other anionic, nonionic, cationic, amphoteric and/or zwitterionic surfactants.

It has surprisingly been found that fatty acid polyglycol ester sulfates with a low degree of alkoxylation, which do not themselves have any pronounced foam properties, represent foam boosters, i.e. synergistically improve the basic foam and the foam stability of other surfactants. The invention includes the observation that these synergistic effects are obtained even in hard water and in the presence of oil (sebum) and apply to a broad range of surfactants. Another advantage of the invention is that the fatty acid polyglycol esters have solubilizing properties and thus improve the formulation of surfactants which would otherwise tend to be poorly soluble in cold water. In addition, the foam boosters show adequate detersive properties so that, in contrast to alkanolamides for example, they make a contribution to the cleaning performance. Finally, the substances are dermatologically safe, readily biodegradable and, of course, free from nitrosamines.

DETAILED DESCRIPTION OF THE INVENTION

Fatty acid polyglycol ester sulfates

Fatty acid polyglycol ester sulfates are produced by sulfation of the corresponding fatty acid polyglycol esters which, in turn, are obtainable by the relevant preparative methods of organic chemistry. To this end, ethylene oxide, propylene oxide or a mixture thereof is added—in random or block distribution—onto the corresponding fatty acids in the presence of an acid as catalyst, but preferably in the presence of bases, for example sodium methylate or calcined hydrotalcite. If a degree of alkoxylation of 1 is required, the intermediate products may also be prepared by esterification of the fatty acids with a corresponding alkylene glycol. The sulfation of the fatty acid polyglycol esters may be carried out in known manner with chlorosulfonic acid or, preferably, gaseous sulfur trioxide, the molar ratio of fatty acid glycol ester to sulfating agent being in the range from 1:0.95 to 1:1.2 and preferably in the range from 1:1 to 1:1.1 and the reaction temperature being in the range from 30 to 80° C and preferably in the range from 50 to 60° C. The fatty acid polyglycol esters may also be undersulfated, i.e. the sulfating agent may be used in far less than the quantity which would be stoichiometrically necessary for a complete reaction. If, for example, the fatty acid polyglycol ester and sulfating agent are used in a molar ratio of 1:0.5 to 1:0.95, mixtures of fatty acid polyglycol ester sulfates and fatty acid polyglycol esters, which are also advantageous for a whole range of applications, are obtained. In order to avoid hydrolysis, it is very important to carry out the neutralization step at a pH value in the range from 5 to 9 and preferably in the range from 7 to 8. Examples of suitable starting materials are the addition products of 1 to 3 moles of ethylene oxide and/or propylene oxide, but preferably the addition products of 1 mole of ethylene oxide or 1 mole of propylene oxide with caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, which are then sulfated and neutralized as described above. A preferred embodiment of the invention is characterized by the use of fatty acid polyglycol ester sulfates corresponding to formula (I), in which $R^1CO$ is an acyl group containing 12 to 18 carbon atoms, x has an average value of 1 or 2, AO represents a $CH_2CH_2O$ group and X is sodium or ammonium, such as for example lauric acid+1EO sulfate sodium salt, lauric acid+1EO sulfate ammonium salt, cocofatty acid+1EO sulfate sodium salt, cocofatty acid+1EO sulfate ammonium salt, tallow fatty acid+1EO sulfate sodium salt, tallow fatty acid+1EO sulfate ammonium salt and mixtures thereof.

Surfactants

The surfactants used may be nonionic, anionic, cationic and/or amphoteric or zwitterionic surfactants. Typical examples of anionic surfactants are soaps, alkylbenzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, amide ether carboxylic acids and salts thereof, fatty acid isethionates, fatty acid sarcosinates, fatty acid taurides, N-acylamino acids such as, for example, acyl lactylates, acyl tartrates, acyl glutamates, acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkylglucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow homolog distribution. Typical examples of cationic surfactants are quaternary tetraalkylammonium compounds and esterquats, more particularly quaternized difatty acid trialkanolamine ester or difatty acid methyl diethanolamine ester salts. Typical examples of amphoteric or zwitterionic surfactants are alkyl betaines, alkylamido betaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217. The detergent mixtures may contain components (a) and (b) in a ratio by weight of 90:10 to 10:90, preferably in a ratio by weight of 75:25 to 25:75 and more preferably in a ratio by weight of 60:40 to 40:60. Preferred binary or ternary combinations are those of lauric acid or cocofatty acid+1EO sulfate sodium or ammonium salt with alkyl ether sulfates, fatty acid monoglyceride sulfates, alkyl oligoglucosides and/or betaines.

COMMERCIAL APPLICATIONS

The fatty acid polyglycol esters corresponding to formula (I) synergistically improve the initial foaming behavior and foam stability of a large number of surfactants, even in the presence of water hardness and oil. Accordingly, the present invention also relates to their use as foam boosters for improving the foam properties of anionic, nonionic, cationic and/or amphoteric or zwitterionic surfactants.

EXAMPLES

In order to investigate foam behavior, 10% by weight aqueous surfactant solutions (21° dH+1% by weight sebum) were prepared and the foam volume was determined to the Standard DIN 53902, Part 1. In this method, the foam is produced by beating the liquid sample in a jar for 30 seconds with a horizontally aligned perforated plate attached to a handle. The foam volume formed is measured immediately after the end of beating and after 1, 5 and 20 minutes. The results are set out in Tables 1 to 3. The following surfactants were used (quantities in % by weight).

A1) Sodium Laureth Sulfate (Texapon® NSO, Henkel KGaA)
A2) Cocomonoglyceride sulfate sodium salt (Plantapon® CMGS, Henkel KGAA)
A3) Laureth-7 ether carboxylic acid sodium salt
A4) Coco Glucosides (Plantacare® APG 1200, Henkel KGaA)
A5) Lauric acid-N-methyl glucamide
A6) Cocamidopropyl Betaine (Dehyton® PK, Henkel KGaA)
B1) Lauric acid+1EO sulfate sodium salt
B2) Cocofatty acid+1EO sulfate ammonium salt

TABLE 1

Foam measurements - binary surfactant mixtures (invention)

| Ex. | Foam height [ml] | A | B | Ratio by weight A:B | | | | |
|---|---|---|---|---|---|---|---|---|
| | | | | 90:10 | 75:25 | 60:40 | 50:50 | 40:60 |
| 1 | Immediately | A1 | B1 | 550 | 600 | 590 | 570 | 540 |
| | After 1 min. | | | 550 | 600 | 590 | 560 | 520 |
| | After 5 mins. | | | 540 | 590 | 580 | 550 | 500 |
| | After 20 mins. | | | 530 | 590 | 570 | 540 | 480 |
| 2 | Immediately | A2 | B1 | 430 | 450 | 430 | 420 | 410 |
| | After 1 min. | | | 400 | 410 | 400 | 390 | 390 |
| | After 5 mins. | | | 370 | 390 | 370 | 350 | 340 |
| | After 20 mins. | | | 330 | 350 | 330 | 320 | 300 |
| 3 | Immediately | A3 | B2 | 420 | 430 | 410 | 400 | 400 |
| | After 1 min. | | | 400 | 400 | 390 | 370 | 350 |
| | After 5 mins. | | | 370 | 370 | 350 | 330 | 320 |
| | After 20 mins. | | | 250 | 270 | 240 | 240 | 230 |
| 4 | Immediately | A4 | B1 | 510 | 530 | 520 | 500 | 490 |
| | After 1 min | | | 500 | 510 | 500 | 490 | 470 |
| | After 5 mins. | | | 480 | 490 | 480 | 470 | 440 |
| | After 20 mins. | | | 450 | 470 | 460 | 440 | 400 |
| 5 | Immediately | A5 | B1 | 500 | 520 | 510 | 500 | 480 |
| | After 1 min. | | | 490 | 500 | 500 | 480 | 460 |
| | After 5 mins. | | | 470 | 470 | 470 | 460 | 430 |
| | After 20 mins. | | | 460 | 450 | 450 | 430 | 390 |
| 6 | Immediately | A6 | B1 | 410 | 430 | 420 | 410 | 400 |
| | After 1 min. | | | 380 | 390 | 370 | 366 | 350 |
| | After 5 mins. | | | 310 | 330 | 320 | 320 | 320 |
| | After 20 mins. | | | 290 | 290 | 290 | 280 | 280 |

TABLE 2

Foam measurements - ternary mixtures (invention)

| Ex. | Foam height [ml] | A | B | C | Ratio by weight A:B | | | |
|---|---|---|---|---|---|---|---|---|
| | | | | | 45:10:45 | 50:10:40 | 40:20:40 | 50:20:30 |
| 7 | Immediately | A1 | B1 | A5 | 630 | 650 | 630 | 630 |
| | After 1 min. | | | | 620 | 640 | 620 | 620 |
| | After 5 mins. | | | | 610 | 630 | 610 | 610 |
| | After 20 mins. | | | | 580 | 600 | 590 | 600 |

TABLE 3

Foam measurements (comparison)

| Ex. | Foam height [ml] | Comparison surfactants (100% by weight) | | | | | | | |
|---|---|---|---|---|---|---|---|---|---|
| | | A1 | A2 | A3 | A4 | A5 | A6 | B1 | B2 |
| C1 | Immediately | 500 | 400 | 390 | 480 | 470 | 390 | 200 | 200 |
| C8 | After 1 min | 470 | 350 | 340 | 450 | 440 | 350 | 150 | 150 |
| | After 5 mins. | 430 | 300 | 300 | 410 | 400 | 310 | 100 | 100 |
| | After 20 mins. | 400 | 250 | 200 | 390 | 380 | 270 | 50 | 50 |

What is claimed is:

1. A high-foaming detergent mixture comprising:
   (a) at least one fatty acid polyglycol ester sulfate of the general formula (1):

$$R^1COO(AO)_xSO_3X \qquad (I)$$

wherein $R^1CO$ represents an acyl group and $R^1$ is selected from the group consisting of linear, branched, saturated and unsaturated chains having from about 6 to about 22 carbon atoms, x is an integer having a value of from 1 to 3, each AO independently represents a $CH_2CH_2O$, $CH_2CH(CH_3)O$ or $CH(CH_3)CH_2O$ group, and X is selected from the group consisting of an alkali metal, an alkaline earth metal, ammonium, an alkylammonium, an alkanolammonium or a glucammonium; and
   (b) at least one additional surfactant selected from the group consisting of anionics, nonionics, cationics, amphoterics and zwitterionics.

2. The detergent mixture according to claim 1, wherein $R^1$ is selected from the group consisting of linear, branched, saturated and unsaturated chains having from about 12 to about 18 carbon atoms, x is an integer having a value of from 1 to 2, each AO represents a $CH_2CH_2O$ group, and X is selected from the group consisting of sodium and ammonium.

3. The detergent mixture according to claim 1, wherein said at least one additional surfactant is an anionic surfactant selected from the group consisting of soaps, alkylbenzenesulfonates, alkanesulfonates, olefin sulfonates, alkylether sulfonates, glycerol ether sulfonates, alpha-methyl ester sulfonates, sulfofatty acids, alkylsulfates, fatty alcohol ether sulfates, glycerol ether sulfates, hydroxy mixed ether sulfates, monoglyceride(ether)sulfates, fatty acid amide(ether)sulfates, mono- and dialkyl sulfosuccinates, mono- and dialkyl sulfosuccinamates, sulfotriglycerides, amide soaps, ether carboxylic acids and salts thereof, amide ether carboxylic acids and salts thereof, fatty acid isethionates, fatty acid sarcosinates, fatty acid taurides, N-acylamino acids, alkyl oligoglucoside sulfates, protein fatty acid condensates and alkyl(ether)phosphates.

4. The detergent mixture according to claim 2, wherein said at least one additional surfactant is an anionic surfactant selected from the group consisting of soaps, alkylbenzenesulfonates, alkanesulfonates, olefin sulfonates, alkylether sulfonates, glycerol ether sulfonates, alpha-methyl ester sulfonates, sulfofatty acids, alkylsulfates, fatty alcohol ether sulfates, glycerol ether sulfates, hydroxy mixed ether sulfates, monoglyceride(ether)sulfates, fatty acid amide(ether)sulfates, mono- and dialkyl sulfosuccinates, mono- and dialkyl sulfosuccinamates, sulfotriglycerides, amide soaps, ether carboxylic acids and salts thereof, amide ether carboxylic acids and salts thereof, fatty acid isethionates, fatty acid sarcosinates, fatty acid taurides, N-acylamino acids, alkyl oligoglucoside sulfates, protein fatty acid condensates and alkyl(ether)phosphates.

5. The detergent mixture according to claim 1, wherein said at least one additional surfactant is a nonionic surfactant selected from the group consisting of fatty alcohol polyglycol ethers, fatty acid polyglycol esters, alkylphenol polyglycol ethers, fatty acid amide polyglycol ethers, fatty amine polyglycol ethers, alkoxylated triglycerides, mixed ethers and mixed formals, partly oxidized alk(en)yl oligolycosides or glucuronic acid derivatives, fatty acid-N-alkylglucamides, protein hydrolyzates, polyol fatty acid esters, sugar esters, sorbitan esters, polysorbates and amine oxides.

6. The detergent mixture according to claim 2, wherein said at least one additional surfactant is a nonionic surfactant selected from the group consisting of fatty alcohol polyglycol ethers, fatty acid polyglycol esters, alkylphenol polyglycol ethers, fatty acid amide polyglycol ethers, fatty amine polyglycol ethers, alkoxylated triglycerides, mixed ethers and mixed formals, partly oxidized alk(en)yl oligolycosides or glucuronic acid derivatives, fatty acid-N-alkylglucamides, protein hydrolyzates, polyol fatty acid esters, sugar esters, sorbitan esters, polysorbates and amine oxides.

7. The detergent mixture according to claim 1, wherein said at least one additional surfactant is a cationic surfactant selected from the group consisting of quaternary tetraalkyl ammonium compounds and esterquats.

8. The detergent mixture according to claim 2, wherein said at least one additional surfactant is a cationic surfactant selected from the group consisting of quaternary tetraalkyl ammonium compounds and esterquats.

9. The detergent mixture according to claim 1, wherein said at least one additional surfactant is an amphoteric or zwitterionic surfactant selected from the group consisting of alkyl betaines, alkyl amidobetaines, aminopropionates, aminoglycinates, imidazolinium betaines and sulfobetaines.

10. The detergent mixture according to claim 2, wherein said at least one additional surfactant is an amphoteric or zwitterionic surfactant selected from the group consisting of alkyl betaines, alkyl amidobetaines, aminopropionates, aminoglycinates, imidazolinium betaines and sulfobetaines.

11. The detergent mixture according to claim 1, wherein components (a) and (b) are present in a weight ratio of from about 90:10 to about 10:90.

12. The detergent mixture according to claim 2, wherein components (a) and (b) are present in a weight ratio of from about 90:10 to about 10:90.

13. The detergent mixture according to claim 3, wherein components (a) and (b) are present in a weight ratio of from about 90:10 to about 10:90.

14. The detergent mixture according to claim 4, wherein components (a) and (b) are present in a weight ratio of from about 90:10 to about 10:90.

15. The detergent mixture according to claim 5, wherein components (a) and (b) are present in a weight ratio of from about 90:10 to about 10:90.

16. The detergent mixture according to claim 6, wherein components (a) and (b) are present in a weight ratio of from about 90:10 to about 10:90.

17. The detergent mixture according to claim 7, wherein components (a) and (b) are present in a weight ratio of from about 90:10 to about 10:90.

18. The detergent mixture according to claim 8, wherein components (a) and (b) are present in a weight ratio of from about 90:10 to about 10:90.

19. The detergent mixture according to claim 9, wherein components (a) and (b) are present in a weight ratio of from about 90:10 to about 10:90.

20. The detergent mixture according to claim 10, wherein components (a) and (b) are present in a weight ratio of from about 90:10 to about 10:90.

21. A method of improving foam properties of surfactants, said method comprising:

(a) combining at least one fatty acid polyglycol ester sulfate of the general formula (I):

$$R^1COO(AO)_xSO_3X \qquad (I)$$

wherein $R^1CO$ represents an acyl group and $R^1$ is selected from the group consisting of linear, branched, saturated and unsaturated chains having from about 6 to about 22 carbon atoms, x is an integer having a value of from 1 to 3, each AO independently represents a $CH_2CH_2O$, $CH_2CH(CH_3)O$ or $CH(CH_3)CH_2O$ group, and X is selected from the group consisting of an alkali metal, an alkaline earth metal, ammonium, an alkylammonium, an alkanolammonium or a glucammonium, with at least one surfactant selected from the group consisting of anionics, nonionics, cationics, amphoterics and zwitterionics.

* * * * *